(12) United States Patent
Oh et al.

(10) Patent No.: US 9,308,117 B2
(45) Date of Patent: Apr. 12, 2016

(54) RING FOR ENHANCING MALE FUNCTIONS

(76) Inventors: Seo Jun Oh, Seoul (KR); Seo Min Oh, Seoul (KR)

( * ) Notice: Subject to any disclaimer, the term of this patent is extended or adjusted under 35 U.S.C. 154(b) by 36 days.

(21) Appl. No.: 14/238,042

(22) PCT Filed: Aug. 10, 2012

(86) PCT No.: PCT/KR2012/006380
§ 371 (c)(1),
(2), (4) Date: Feb. 10, 2014

(87) PCT Pub. No.: WO2013/022303
PCT Pub. Date: Feb. 14, 2013

(65) Prior Publication Data
US 2014/0179996 A1    Jun. 26, 2014

(30) Foreign Application Priority Data
Aug. 10, 2011    (KR) .................. 10-2011-0079865

(51) Int. Cl.
*A61F 5/00*    (2006.01)
*A61F 5/41*    (2006.01)

(52) U.S. Cl.
CPC ............. *A61F 5/41* (2013.01); *A61F 2005/414* (2013.01)

(58) Field of Classification Search
CPC ............................. A61F 5/41; A61F 2005/414
USPC ....................................................... 600/38–41
See application file for complete search history.

(56) References Cited

U.S. PATENT DOCUMENTS 5,810,710 A *   9/1998   Burgos ............................ 600/41
2002/0137983 A1   9/2002   Chen

FOREIGN PATENT DOCUMENTS

| KR | 20-0200624 Y1 | 10/2000 |
| KR | 20-0230061 Y1 | 5/2001 |
| KR | 10-2005-0062761 | 6/2005 |
| WO | WO 2013/022303 A2 | 2/2013 |

OTHER PUBLICATIONS

PCT International Search Report dated Feb. 26, 2013, issued in corresponding International Application No. PCT/KR2012/006380 (5 pages).
PCT International Preliminary Report on Patentability dated Feb. 20, 2014, issued in corresponding International Application No. PCT/KR2012/006380 (12 pages).

\* cited by examiner

*Primary Examiner* — John Lacyk
(74) *Attorney, Agent, or Firm* — Finnegan, Henderson, Farabow, Garrett & Dunner, LLP

(57) ABSTRACT

The present invention relates to a ring for enhancing male functions, and comprises: a first sectioned ring member; a second sectioned ring member having one end portion which is rotatably coupled to one end portion of the first sectioned ring member; and a coupling member, which is rotatably provided on the other end portion of the second sectioned ring member, and which couples to the other end portion of the first sectioned ring member so as to be separable, wherein the coupling member comprises a coupling plate, which is hinged-coupled to the other end of the second sectioned ring member, and a stopper protrusion portion that is protrudingly formed on the inner surface of the coupling plate, and wherein the first sectioned ring member comprises, on the other end portion thereof, a groove portion, and a hooking rod, which is provided on the groove, for coupling to the stopper protrusion by means of hooking.

8 Claims, 7 Drawing Sheets

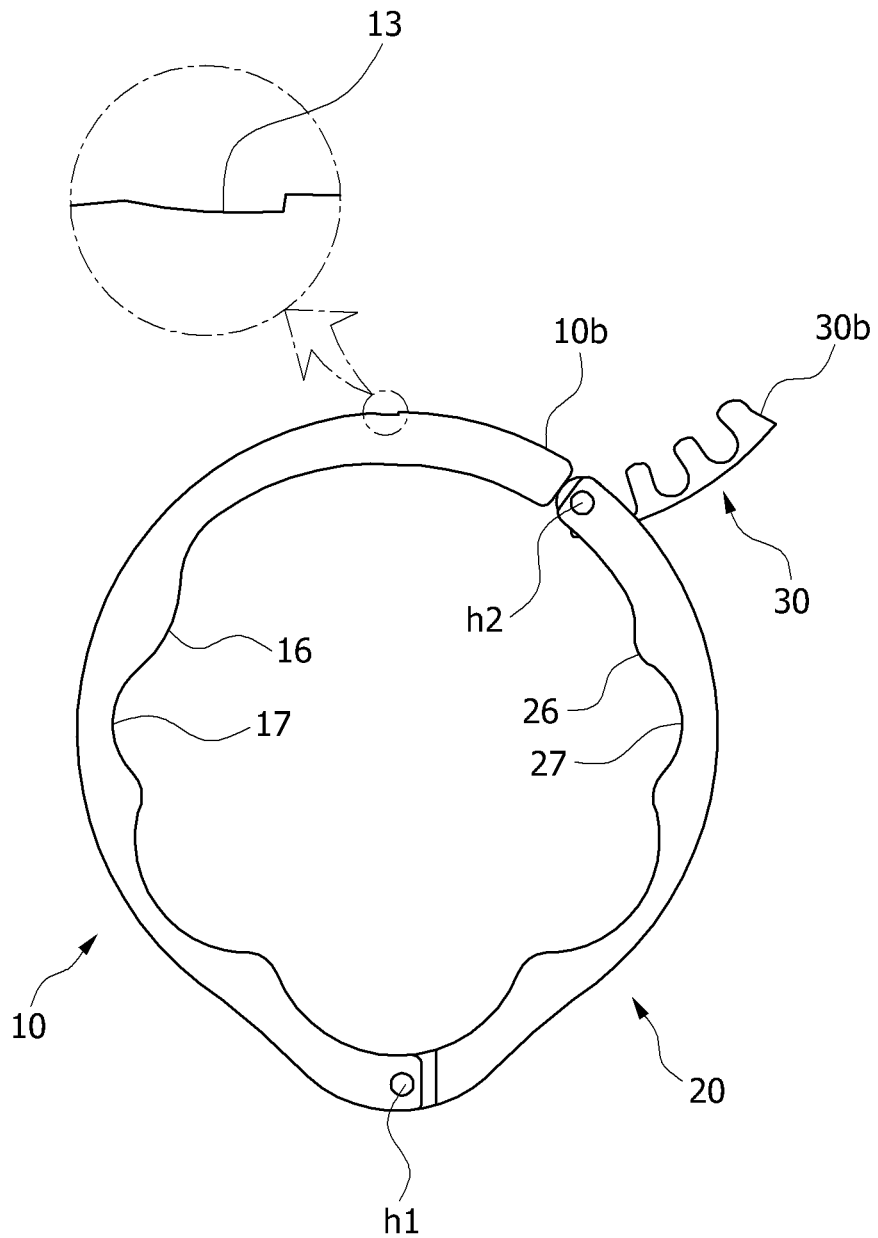

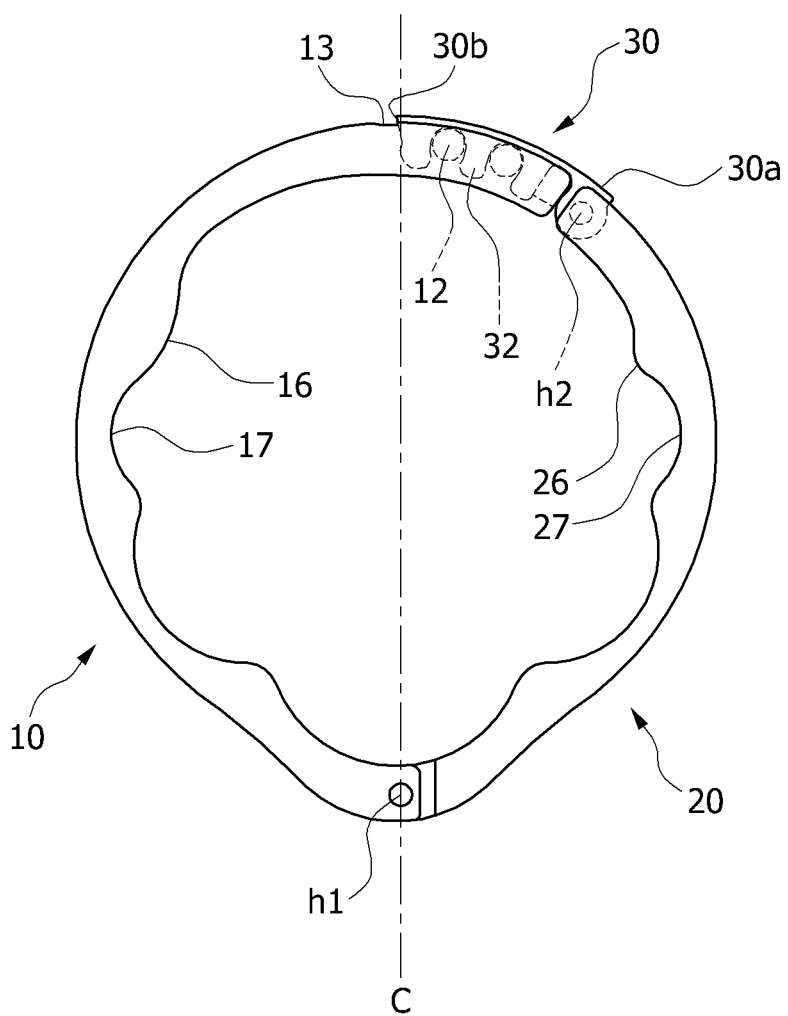

RING FOR ENHANCING MALE FUNCTIONS

CROSS REFERENCE TO RELATED APPLICATIONS

This application is a national stage application of International Patent Application No. PCT/KR2012/006380, entitled "Ring for Enhanced Male Functions," filed on Aug. 10, 2012, which claims priority to Korean Application No. 10-2011-0079865, filed on Aug. 10, 2011, the entire contents of which are incorporated herein by reference in their entirety.

TECHNICAL FIELD

The present invention relates to a ring for enhancing male functions and, more particularly, to a ring for enhancing male functions which can rapidly fasten and release ring segment members, strengthen erection while preventing separation of the ring, and prolong a sexual act by preventing premature ejaculation.

BACKGROUND

In general, erection of a penis is brought about by collective interaction of components of the endocrine system including nerves, blood vessels, the testes, and pituitary gland hormones, and the penis has a special structure to react to this process. The penis is formed of a cavernous body tissue, such as a sponge, including a number of blood vessels. When sexual stimuli including visual, aural, and tactile stimuli are applied, the blood vessels in the penis expand, a large amount of blood flows into the penis, and then the penis expands by blood pressure to become erect. Recently, due to complexities of social environments and stress from heavy workloads, however, a number of men suffer from erectile dysfunction and premature ejaculation preventing a normal sex life.

A background technique of the present invention is disclosed in Korean Patent Publication No. 2002-0043418 (published on Jun. 10, 2002 and entitled "Male function enhancement Ring").

Since most male function enhancement rings sold in the market do not have an opening/closing device, a user must wait until erection subsides to remove the ring, or even when there is an opening/closing device, it is very difficult to open the ring. Accordingly, it is difficult to open the ring during full erection or a user must suspend a sexual act and wait until the erection subsides to open the ring. In addition, the opening/closing device of a typical male function enhancement ring is often unintentionally opened, causing user discomfort. Further, the typical male function enhancement ring has a limit in that when the penis becomes flaccid after the ring is fitted into the penis, the ring is likely to be lost due to separation from the penis.

Therefore, there is a need to solve such problems in the art.

SUMMARY

The present invention has been made to solve such problems in the art, and an aspect of the present invention is to provide a ring for enhancing male functions, which can rapidly fasten and release ring segment members and enables erection to be strengthened and prolonged for a long period of time by constricting the penis in stages even when the penis is not fully erect.

In accordance with one aspect of the present invention, a ring for enhancing male functions includes: a first ring segment member; a second ring segment member rotatably coupled at one end thereof to one end of the first ring segment member; and a fastening member rotatably provided to the other end of the second ring segment member and removably coupled to the other end of the first ring segment member, wherein the fastening member includes: a fastening plate hingedly coupled to the other end of the second ring segment member and a latch protrusion protruding from an inner surface of the fastening plate, and the first ring segment member includes a recess formed at the other end thereof and a latch rod disposed in the recess to be latched to the latch protrusion.

The fastening plate may include a plurality of latch protrusions protruding from the inner surface thereof, and the first ring segment member may include a plurality of latch rods disposed in the recess to be latched to the latch protrusions, respectively.

The fastening plate may cover the recess such that the recess is not exposed outside when the latch protrusion is latched to the latch rod.

The recess may be formed on an outer circumferential surface of the first ring segment member, and the fastening plate may cover the recess from above the recess.

The first ring segment member may further include a guide inclined surface formed on the outer circumferential surface thereof adjoining the recess.

The first ring segment member may further include a location checking portion formed on the other end thereof for informing of a direction in which the fastening member is latched to the first ring segment member.

The location checking portion may be formed of a different material or color than that of the first ring segment member.

The first and second ring segment members may form a ring shape when the latch protrusion is latched to the latch rod.

The first ring segment member may further include a plurality of first bosses protruding inward from an inner circumferential surface thereof and a first groove formed between adjacent first bosses, and the second ring segment member may further include a plurality of second bosses protruding inward from an inner circumferential surface thereof and a second groove formed between adjacent second bosses.

Each of the first and second bosses may have a greater slope from a rear end to a highest protruding point than a slope from a front end to the highest protruding point.

In accordance with another aspect of the present invention, a ring for enhancing male functions includes: a first ring segment member; a second ring segment member rotatably coupled at one end thereof to one end of the first ring segment member; and a fastening member, one end of which is rotatably provided to the other end of the second ring segment member and the other end of which is removably coupled to the other end of the first ring segment member, wherein the other end of the fastening member is located at a central portion of a ring shape formed by the first and second ring segment members when the fastening member is coupled to the other end of the first ring segment member.

The first and second ring segment members may be coupled to each other through a hinge, and a straight line connecting the hinge to the other end of the fastening member may form a centerline of the ring shape formed by the first and second ring segment members.

The first ring segment member may further include a guide inclined surface formed on the outer circumferential surface thereof adjoining the other end of the fastening member.

The first ring segment member may further include a location checking portion formed on the other end thereof for informing of a direction in which the fastening member is latched to the first ring segment member.

The fastening member may include a fastening plate hingedly coupled to the other end of the second ring segment member and a latch protrusion protruding from an inner surface of the fastening plate, and the first ring segment member may include a recess formed at the other end thereof and a latch rod disposed in the recess to be latched to the latch protrusion.

The first ring segment member may further include a plurality of first bosses protruding inward from an inner circumferential surface thereof and a first groove formed between adjacent first bosses, and the second ring segment member may further include a plurality of second bosses protruding inward from an inner circumferential surface thereof and a second groove formed between adjacent second bosses.

Each of the first and second bosses may have a greater slope from a rear end to a highest protruding point than a slope from a front end to the highest protruding point.

In accordance with a further aspect of the present invention, a ring for enhancing male functions includes: a first ring segment member having a first boss protruding inward from an inner circumferential surface thereof; a second ring segment member rotatably coupled at one end thereof to one end of the first ring segment member and having a second boss protruding inward from an inner circumferential surface thereof; and a fastening member rotatably provided to the other end of the second ring segment member and detachably coupled to the other end of the first ring segment member.

The first ring segment member may include a plurality of first bosses formed on the inner circumferential surface thereof and a first groove formed between adjacent first bosses, and the second ring segment member may include a plurality of second bosses formed on the inner circumferential surface and a second groove formed between adjacent second bosses.

Each of the first and second bosses may have a highest protruding point that is biased from a center thereof toward a rear end thereof.

Each of the first and second bosses may have a greater slope from a rear end to the highest protruding point than a slope from a front end to the highest protruding point.

In accordance with yet another aspect of the present invention, a ring for enhancing male functions includes: a first ring segment member; a second ring segment member rotatably coupled at one end thereof to one end of the first ring segment member; and a fastening member, one end of which is rotatably provided to the other end of the second ring segment member and the other end of which is removably coupled to the other end of the first ring segment member, wherein the other end of the fastening member is located at a central portion of a ring shape formed by the first and second ring segment members when the fastening member is coupled to the other end of the first ring segment member, wherein the fastening member includes a fastening plate hingedly coupled to the other end of the second ring segment member and a latch protrusion protruding from an inner surface of the fastening plate, and the first ring segment member includes a recess formed at the other end thereof and a latch rod disposed in the recess to be latched to the latch protrusion, wherein the first ring segment member further includes a plurality of first bosses protruding inward from an inner circumferential surface thereof and a first groove formed between adjacent first bosses, and the second ring segment member further includes a plurality of second bosses protruding inward from an inner circumferential surface thereof and a second groove formed between adjacent second bosses, and wherein each of the first and second bosses may have a greater slope from a rear end to a highest protruding point than a slope from a front end to the highest protruding point.

In accordance with yet another aspect of the present invention, a ring for enhancing male functions includes: a first ring segment member; a second ring segment member rotatably coupled at one end thereof to one end of the first ring segment member; and a fastening member, one end of which is rotatably provided to the other end of the second ring segment member and the other end of which is removably coupled to the other end of the first ring segment member, wherein the first and second ring segment members are mutually asymmetrically formed when the fastening member is coupled to the other end of the first ring segment member such that the first and second ring segment members form a ring shape.

According to the present invention, a ring for enhancing male functions is mounted on the penis and may be rapidly removed so as to reduce an accident occurring in an emergency, and can reduce aching and delay ejaculation when the highest state of sexual arousal and erection are reached.

Further, according to the present invention, a ring for enhancing male functions applies continuous pressure to the penis by bosses formed on the inner perimeter of the ring, whereby erection can be strengthened through pressure from the bosses even on an initially flaccid penis, and duration of the erection can be lengthened.

Furthermore, according to the present invention, inclined slopes of bosses formed on the inner perimeter of a ring for enhancing male functions are different at the front end and the read end, so that the ring for enhancing male functions can be prevented from falling off the penis, and since the ring for enhancing male functions may only be moved toward the base of the penis, the ring can be prevented from falling off the glans.

BRIEF DESCRIPTION OF DRAWINGS

FIG. 6 is a view of the ring for enhancing male functions according to the embodiment of the present invention, showing a state in which first and second ring segment members are coupled to each other; and FIG. 7 is a view of the ring for enhancing male functions according to the embodiment of the present invention, showing a state in which the fastening member is coupled to the first ring segment member.

DETAILED DESCRIPTION

Hereinafter, exemplary embodiments of the present invention will be described with reference to the accompanying drawings.

It should be noted that the drawings are not to precise scale and may be exaggerated in thickness of lines or size of components for descriptive convenience and clarity only.

Furthermore, terms used herein are defined by taking functions of the present disclosure into account and can be changed according to the custom or intention of users or operators.

Therefore, definition of the terms should be made according to the overall disclosure set forth herein.

Figure 1:
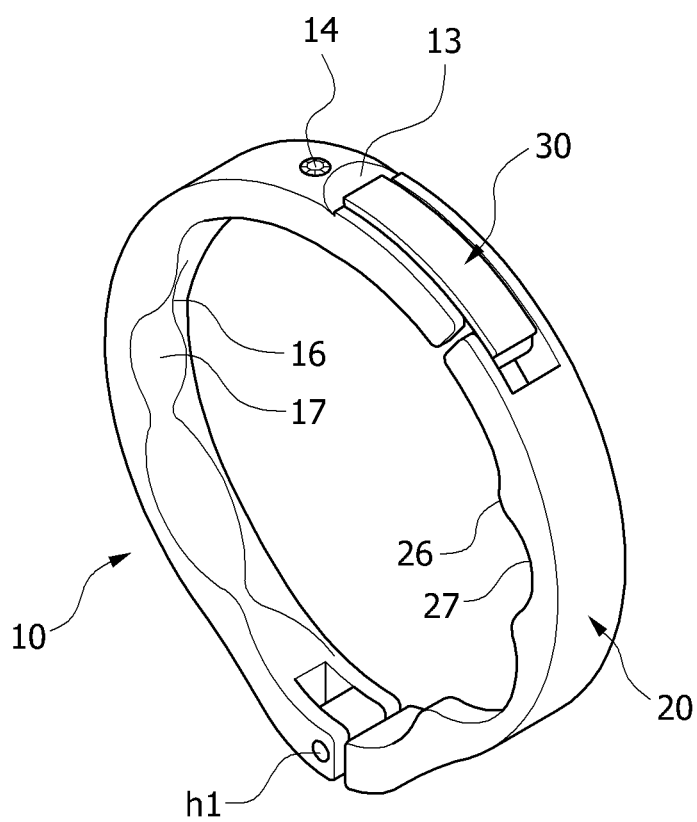
FIG. 1 is a perspective view of a ring for enhancing male functions according to one embodiment of the present invention.
Figure 2:
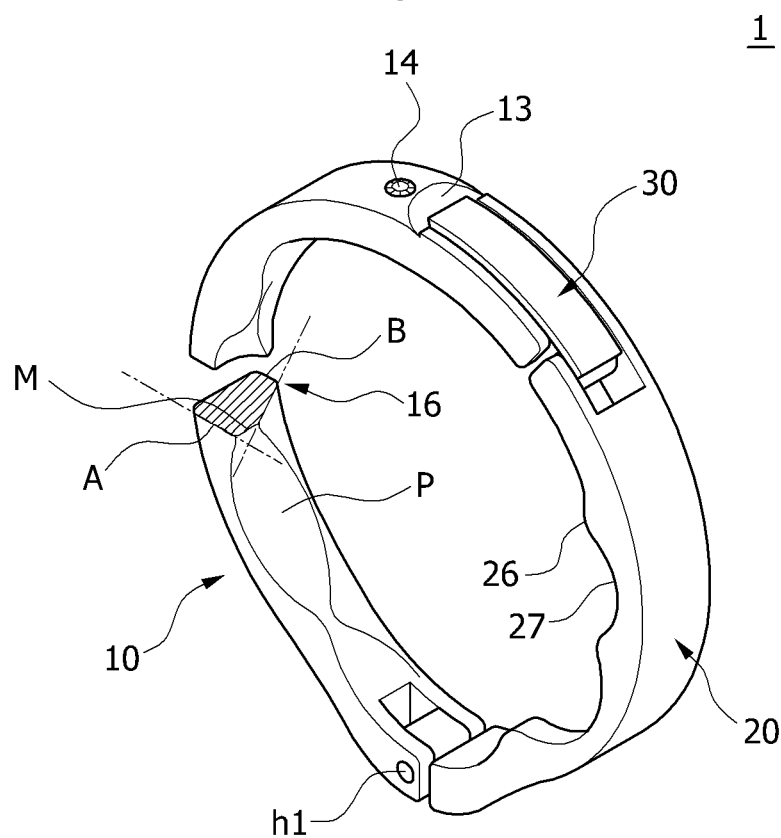
FIG. 2 shows a cross section of a first boss of the ring for enhancing male functions according to the embodiment of the present invention.
Figure 3:
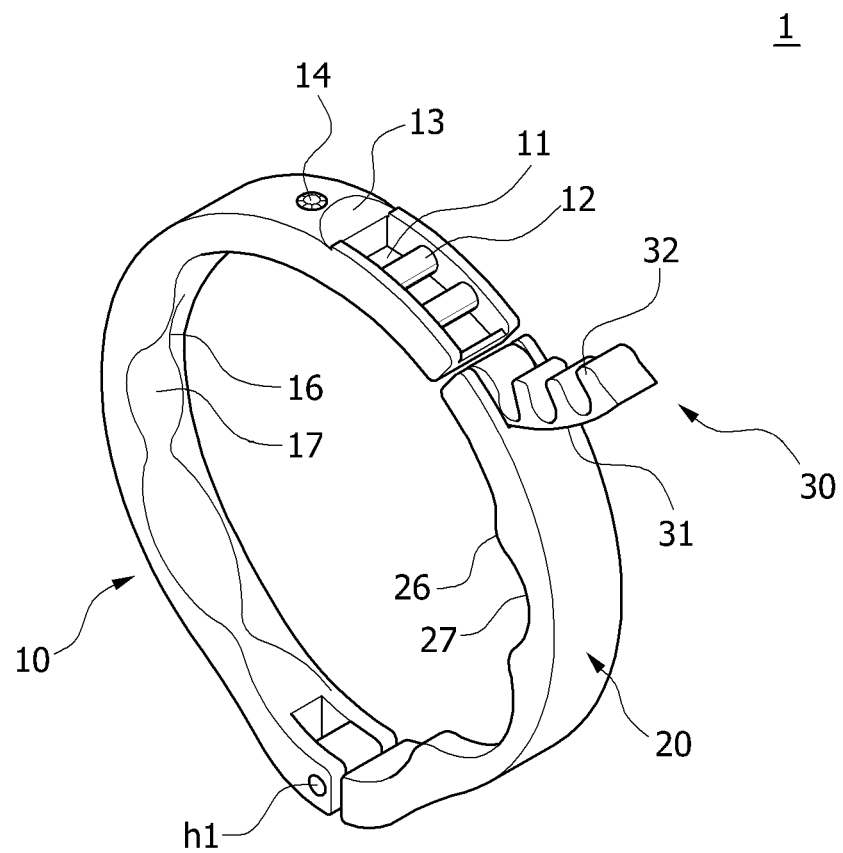
FIG. 3 is a perspective view of the ring for enhancing male functions according to the embodiment of the present invention before a fastening member is coupled to a first ring segment member.
Figure 4:
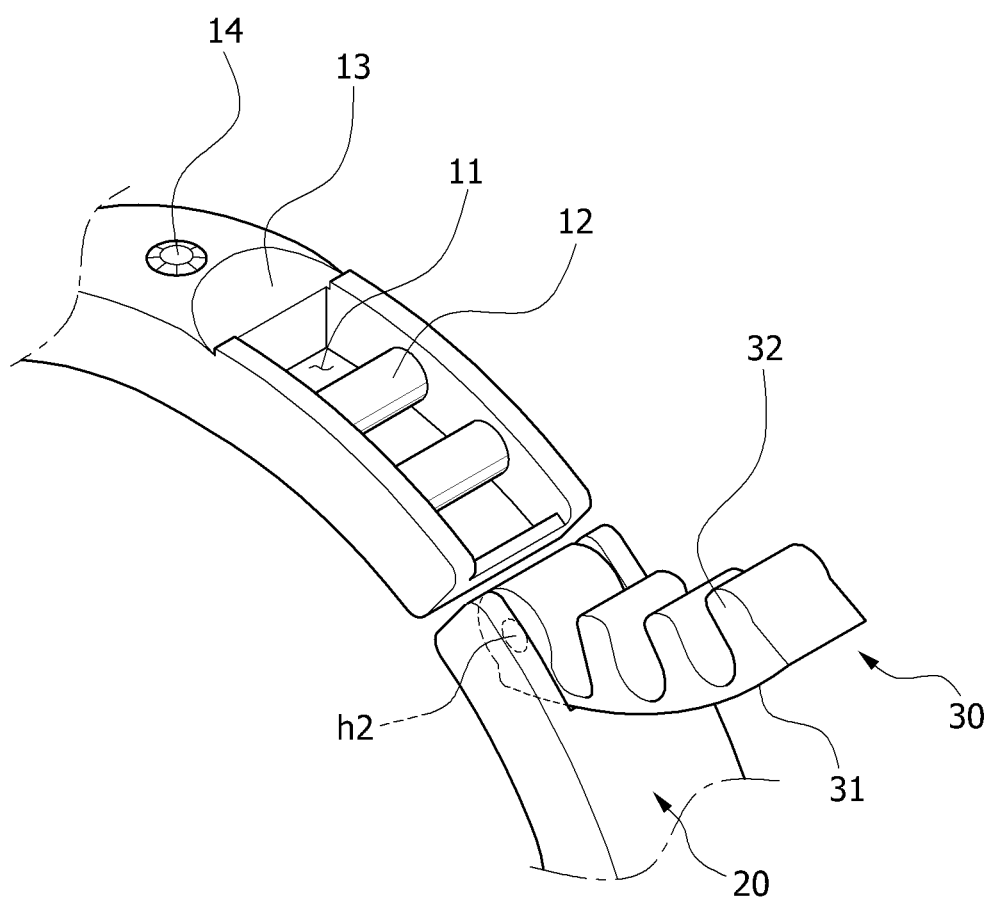
FIG. 4 is an enlarged view of the fastening member and the first ring segment member shown in FIG. 3.
Figure 5:
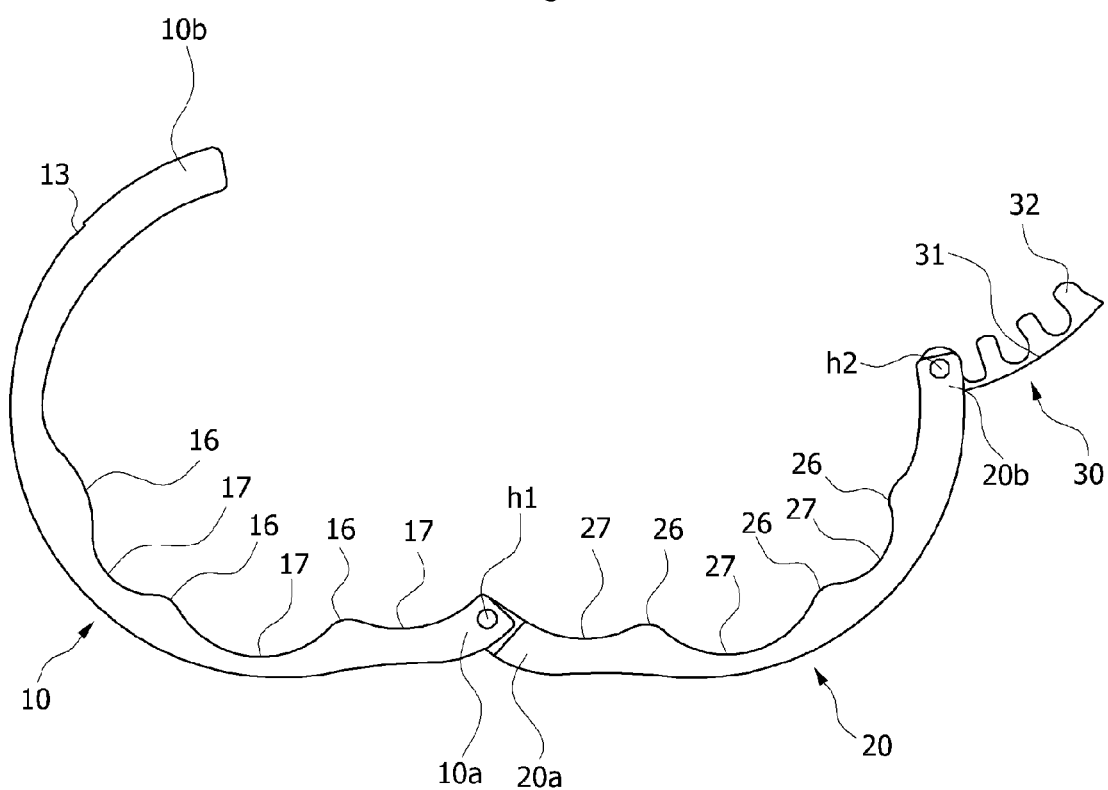
FIG. 5 is a view of the ring for enhancing male functions according to the embodiment of the present invention, showing a state in which first and second ring segment members are drawn apart from each other.

FIG. 1 is a perspective view of a ring for enhancing male functions according to one embodiment of the present invention; FIG. 2 shows a cross section of a first boss of the ring for enhancing male functions according to the embodiment of the present invention; FIG. 3 is a perspective view of the ring for enhancing male functions according to the embodiment of the present invention before a fastening member is coupled to a first ring segment member; FIG. 4 is an enlarged view of the fastening member and the first ring segment member shown in FIG. 3; FIG. 5 is a view of the ring for enhancing male functions according to the embodiment of the present invention, showing a state in which first and second ring segment members are drawn apart from each other; FIG. 6 is a view of the ring for enhancing male functions according to the embodiment of the present invention, showing a state in which first and second ring segment members are coupled to each other; and FIG. 7 is a view of the ring for enhancing male functions according to the embodiment of the present invention, showing a state in which the fastening member is coupled to the first ring segment member.

Referring to FIGS. 1 to 7, a ring 1 for enhancing male functions according to one embodiment of the present invention includes a first ring segment member 10, a second ring segment member 20, and a fastening member 30. The ring 1 has a ring shape and is divided into the first and second ring segment members 10, 20.

The first ring segment member 10 forms one part (a left part in FIG. 1) of the ring 1, and the second ring segment member 20 forms the other part (a right part in FIG. 1) of the ring 1.

The fastening member 30 is provided to the second ring segment member 20 to be removably fastened to the first ring segment member 10. When the fastening member 30 is fastened to the first ring segment member 10, the first and second ring segment members 10, 20 form a ring shape.

One end 10a of the first ring segment member 10 is hingedly coupled to one end 20a of the second ring segment member 20. Thus, the first and second ring segment members 10, 20 are coupled to each other to be rotated about a hinge h1.

The first segmented ring portion 10 has a recess 11 formed at the other end 10b thereof. The recess 11 is formed on an outer circumferential surface of the first ring segment member 10. According to the present embodiment, the recess 11 is closed at both sides and at a lower side thereof, and is open at an upper side thereof to be formed in a ⊔ shape.

The lower side of the recess 11 is closed. Accordingly, the penis cannot press the fastening member 30 even when the penis becomes erect with the ring 1 worn on the penis, thereby preventing the fastening member 30 from being unintentionally separated from the first ring segment member 10.

Latch rods 12 latched to latch protrusions 32 described below are arranged in the recess 11. The latch rods 12 are formed in a shape of a cylindrical column connecting the sidewalls of the recess 11 facing each other and are arranged to be separated from each other.

The one end 20a of the second ring segment member 20 is coupled to the first ring segment member 10, and the other end of 20b of the second ring segment member 20 is hingedly coupled to one end 30a of the fastening member 30. Thus, the fastening member 30 is provided to be rotated about a hinge h2 relative to the second ring segment member 20.

When the fastening member 30 is coupled to the other end 10b of the first ring segment member 10 while rotating about the hinge h2 (see FIG. 7) in a state in which the other end 10b of the first ring segment member 10 and the other end 20b of the second ring segment member 20 contact each other (see FIG. 6), the first and second ring segment members 10, 20 form a ring shape.

The fastening member 30 includes a fastening plate 31 and the latch protrusions 32. The fastening plate 31 is coupled to the other end 20b of the second ring segment member 20 through the hinge h2. An outer surface of the fastening plate 31 has the same smooth surface as the first and second ring segment members 10, 20.

The latch protrusions 32 protrude from an inner surface of the fastening plate 31 and are latched to the latch rods 12. According to the present embodiment, the latch rods 12 are formed in the shape of a cylindrical column, whereby the latch protrusions 32 contacting the latch rods 12 have a curved shape.

A plurality of latch protrusions 32 is arranged separated from each other. The plural latch protrusions 32 are latched to the latch rods 12 while being individually inserted into spaces defined between adjacent latch rods 12.

The fastening member 30 and the first ring segment member 10 are fastened at a plurality of locations through the plurality of latch protrusions 32 and latch rods 12. Accordingly, when the penis becomes erect while the ring 1 is worn on the penis, or external force is applied to the ring 1, the fastening member 30 is prevented from being unintentionally separated from the first ring segment member 10. As described above, according to the present embodiment, the fastening member 30 is separated from the first ring segment member 10 only when the latch protrusions 32 and the latch rods 12 are all released at a plurality of locations, thereby improving coupling strength between the fastening member 30 and the first ring segment member 10.

When the latch protrusions 32 are latched to the latch rods 12, the fastening plate 31 covers the recess 11 such that the recess 11 is not exposed to the outside.

According to the present embodiment, since the recess 11 is formed on the outer circumferential surface of the first ring segment member 10, the fastening plate 31 that rotates about the hinge h2 covers the recess 11 from above the recess 11. Thus, the fastening plate 31 may prevent foreign substances from being introduced into the recess 11.

A guide inclined surface 13 is formed on the outer circumferential surface of the first ring segment member 10. The guide inclined surface 13 is formed on a portion of the outer circumferential surface of the first ring segment member 10 adjoining the recess 11 and guides a user's finger nail to the other end 30b of the fastening member 30.

When separating the fastening member 30 from the first ring segment member 10, a user separate the other end 30b of the fastening member 30 from the other end 10b of the first ring segment member 10 such that the latch protrusions 32 and the latch rods 12 are released.

The guide inclined surface 13 slopes to the recess 11 to allow a thumbnail of a user's right hand to easily reach the other end 30b of the fastening member 30. When the nail of the user is attached to the other end 30b of the fastening member 30, the user lifts the other end 30b of the fastening member 30 using the fingernail. When the other end 30b of the fastening member 30 is separated from the first ring segment member 10, the fastening member 30 rotates about the hinge h2 in the clockwise direction (see FIG. 6).

When the fastening member 30 and the first ring segment member 10 are released as described above, the user can easily remove the ring 1 from the penis.

The first ring segment member 10 is provided with a location checking portion 14 on the outer circumferential surface thereof. The location checking portion 14 is disposed close to the guide inclined surface 13. A user may rapidly recognize the other end 30b of the fastening member 30 through the location checking portion 14.

Since a user can remove the penis confined by the first and second ring segment members 10, 20 from the ring by separating the other end 30b of the fastening member 30 from the first ring segment member 10, it is very important to rapidly recognize the location of the other end 30b of the fastening member 30 in various emergency situations.

The location checking portion 14 is formed of a different material or color than that of the first ring segment member 10. According to the present embodiment, the first ring segment member 10 is formed of silver and thus the location checking portion 14 may be formed of cubic zirconia or plastic having the feeling of a material completely different from that of the first ring segment member 10.

Further, the location checking portion 14 may be formed in a red or blue color different from the inherent color of silver. As the location checking portion 14 is contrasted with the first ring segment member 10, a user can more rapidly discover the location of the other end 30b of the fastening member 30 through the location checking portion 14.

When the fastening member 30 is coupled to the first ring segment member 10, the other end 30b of the fastening member 30 is located at a central portion of the ring formed by the first and second ring segment members 10, 20.

When the fastening member 30 is coupled to the other end of the first ring segment member 10 such that the first and second ring segment members 10, 20 form the ring shape, the first and second ring segment members 10, 20 are mutually asymmetrically formed.

The hinge h1 is located at a lower central portion of the ring formed by the first and second ring segment members 10, 20, and the other end 30b of the fastening member 30 is located at an upper central portion of the ring shape formed by the first and second ring segment members 10, 20. In other words, a straight line C connecting the hinge h1 and the other end 30b of the fastening member 30 forms a centerline of the ring shape formed by the first and second ring segment members 10, 20, namely, the ring 1.

Since the other end 30b of the fastening member 30 is not biased to one side of the ring 1 and is disposed at the upper central portion of the ring, a user may easily separate the other end 30b of the fastening member 30 from the first ring segment member 10 with weak force.

Specifically, when the other end 30b of the fastening member 30 is located at the upper central portion as in the present embodiment, the fastening member 30 can be easily separated from the first ring segment member 10 by using the thumbnail of the right hand. However, when the other end 30b of the fastening member 30 is biased to one side such as a left or right side instead of the central portion, there is difficulty separating the fastening member 30 from the first ring segment member 10 using the thumbnail of the right hand. That is, separation of the fastening member 30 using the thumbnail of the left hand entails awkwardness of the nail direction, and separation of the fastening member 30 using the fingernail of the left hand index finger is not performed with ease since force of the index finger is weak and the fingernail is also weak. Accordingly, separation of the fastening member 30 can be most easily performed when the other end 30b of the fastening member 30 is located at the upper central portion of the ring.

First bosses 16 protrude inward from an inner circumferential surface of the first ring segment member 10. In the present embodiment, the first bosses 16 protrude inward by about 2 mm to 3 mm from the inner circumferential surface. A plurality of first bosses 16 is formed on the inner circumferential surface of the first ring segment member 10 and a first groove 17 is formed between adjacent first bosses 16.

The first boss 16 and the first groove 17 adjoin each other on the inner circumferential surface of the first ring segment member 10 to form a wave shape.

Second bosses 26 protrude inward from an inner circumferential surface of the second ring segment member 20. In the present embodiment, the second bosses 26 protrude inward by about 2 mm to 3 mm from the inner circumferential surface. A plurality of second bosses 26 is formed on the inner circumferential surface of the second ring segment member 20 and a second groove 27 is formed between adjacent second bosses 26.

The second boss 16 and the second groove 17 adjoin each other on the inner circumferential surface of the second ring segment member 20 to form a wave shape.

While the first and second ring segment members 10, 20 are fitted with the penis, the fastening member 30 is coupled to the first ring segment member 10, as shown in FIG. 7.

As the first bosses 16 protrude from the inner circumferential surface of the first ring segment member 10 and the second bosses 26 protrude from the inner circumferential surface of the second ring segment member 20, the penis contacts the first and second bosses 16 and 26 even in a flaccid state. Thus, the ring 1 does not separate from the penis even when the penis is completely flaccid. This means that the ring 1 does not separate from the penis even in a situation, such as walking, in which impact is not applied, and thus, the ring 1 can be previously prevented from being lost when worn on the penis.

The penis is stimulated by contact with the first and second bosses 16 and 26, and is thus more likely to become erect as compared with when not stimulated.

As erection progresses, the penis is expanded toward the first and second grooves 17, 27, whereby the thickness of the penis is further increased. Thereafter, pressure on the cavernous body of the penis increases, thereby strengthening erection, so that erection of the penis is much larger and stronger as compared with when the ring 1 is not used. Further, even when erection is maintained for a long period of time, the penis will not become flaccid. These effects can be more potently realized when the ring is continuously worn even at normal times in order to increase erection strength.

A highest protruding point M where the first boss 16 most highly protrudes inward is biased from a center to a rear end A of a cross section of the first boss 16. With reference to FIG. 2, the highest protruding point M of the first boss 16 is located closer to the rear end A than a front end B.

For the first boss 16, a slope from the rear end A to the highest protruding point M is greater than a slope from the front end B to the highest protruding point M. This prevents the ring 1 worn on the penis from being separated from the penis unless intended by a user.

The ring 1 for enhancing male functions is fitted with the penis such that the rear end A thereof faces towards the base of the penis and the front end B orients towards the glans.

Since the slope from the front end B to the highest protruding point M is relatively moderate in the first boss 16, the ring 1 can be easily fitted with the penis towards the root of the penis. On the other hand, since the slope from the rear end A to the highest protruding point M is relatively steep in the first boss 16, it is difficult for the ring 1 to move towards the glans. Accordingly, the ring 1 moves toward the glans to be prevented from separating from the penis.

In the present embodiment, the inner surface of the ring 1 is formed to be symmetric with respect to the centerline C. Accordingly, like the first boss 16, a highest protruding point where the second boss 26 most highly protrudes inward is biased from a center to a rear end of a cross section of the second boss 26. The highest protruding point of the second boss 26 is located closer to the rear end than a front end.

For the second boss 26, a slope from the rear end to the highest protruding point is greater than a slope from the front end to the highest protruding point. This prevents the ring 1 worn on the penis from being separated from the penis unless intended by a user.

Since the slope from the front end to the highest protruding point is relatively moderate in the second boss 26, the ring 1 is easily fitted with the penis towards the base of the penis. On the other hand, since the slope from the rear end to the highest protruding point is relatively steep in the second boss 26, it is difficult for the ring 1 to move towards the glans. Accordingly, the ring 1 moves toward the glans to be prevented from separation from the penis.

A smooth surface portion P is formed on the inner surface of the ring 1 on which the first bosses 16, the first grooves 17, the second boss 26, and the second grooves 27 are formed. Accordingly, even when the inner surface of the ring 1 is formed in a concave-convex pattern, the penis can be prevented from being injured by a scratch due to the ring 1.

Although some embodiments have been described herein, it should be understood by those skilled in the art that various modifications, changes, and alterations can be made without departing from the spirit and scope of the invention.

Therefore, the scope of the invention should be limited only by the accompanying claims and equivalents thereof.

The invention claimed is:

1. A ring for enhancing male functions, comprising:
a first ring segment member comprising a plurality of first bosses protruding inward from a first inner circumferential surface thereof and a first groove formed between adjacent first bosses, the adjacent first bosses and the first groove adjoining each other on the first inner circumferential surface to form a wave shape, at least one of the first bosses including a first slope from a first rear end towards a root of a penis to a first protruding point and a second slope from a first front end towards glans to the first protruding point, the first slope being greater than the second slope, and the first protruding point being located closer to the first rear end than to the first front end;
a second ring segment member rotatably coupled at a first end thereof to a first end of the first ring segment member, the second ring segment comprising a plurality of second bosses protruding inward from a second inner circumferential surface thereof and a second groove formed between adjacent second bosses, the adjacent second bosses and the second groove adjoining each other on the second inner circumferential surface to form a wave shape, at least one of the second bosses including a third slope from a second rear end towards the root of the penis to a second protruding point and a fourth slope from a second front end towards the glans to the second protruding point, the third slope being greater than the fourth slope, and the second protruding point being located closer to the second rear end than to the second front end;
and
a fastening member rotatably provided to a second end of the second ring segment member and removably coupled to a second end of the first ring segment member, the first ring segment further comprising a recess formed on an outer circumferential surface at the second end of the first ring segment and a plurality of latch rods in the outer circumferential surface of the recess, each of the plurality of latch rods being separated from each other;
wherein the fastening member comprises a fastening plate hingedly coupled to the second end of the second ring segment member at a hinge, the fastening plate being rotatable about the hinge when the second end of the first ring segment member is in contact with the second end of the second ring segment member to form a ring shape;
wherein the fastening plate comprises a plurality of latch protrusions protruding from an inner surface thereof, each of the latch protrusions being separated from each other and being configured to latch, respectively, with each of the plurality of latch rods of the first ring segment;
wherein the fastening plate is configured to cover the recess such that the recess is not exposed when the latch protrusions are latched to the latch rods.

2. The ring for enhancing male functions according to claim 1, wherein the first ring segment member further comprises a guide inclined surface formed on the outer circumferential surface thereof adjoining the recess.

3. The ring for enhancing male functions according to claim 1, wherein the first ring segment member further comprises a location checking portion formed on the second end thereof for informing of a direction in which the fastening member is latched to the first ring segment member.

4. The ring for enhancing male functions according to claim 3, wherein the location checking portion is formed of a different material or color than that of the first ring segment member.

5. The ring for enhancing male functions according to claim 1, wherein the first and second ring segment members form a ring shape when the latch protrusions are latched to the latch rods.

6. A ring for enhancing male functions, comprising:
a first ring segment member comprising a plurality of first bosses protruding inward from a first inner circumferential surface thereof and a first groove formed between adjacent first bosses, the adjacent first bosses and the first groove adjoining each other on the first inner circumferential surface to form a wave shape, at least one of the first bosses including a first slope from a first rear end towards a root of a penis to a first protruding point and a second slope from a first front end towards glans to the first protruding point, the first slope being greater than the second slope, and the first protruding point being located closer to the first rear end than to the first front end;
a second ring segment member rotatably coupled at a first end thereof to a first end of the first ring segment member through a first hinge, the second ring segment comprising a plurality of second bosses protruding inward from a second inner circumferential surface thereof and a second groove formed between adjacent second bosses, the adjacent second bosses and the second groove adjoining each other on the second inner circumferential surface to form a wave shape, at least one of the second bosses including a third slope from a second rear end towards the root of the penis to a second protruding point and a fourth slope from a second front end towards the glans to the second protruding point, the third slope being greater than the fourth slope, and the second protruding point being located closer to the second rear end than to the second front end;
and
a fastening member, a first end of which is rotatably provided to a second end of the second ring segment member and a second end of which is removably coupled to a second end of the first ring segment member, wherein the second end of the fastening member is located at a central portion of a ring shape formed by the first and second ring segment members when the fastening member is coupled to the second end of the first ring segment member, the first ring segment further comprising a recess formed on an outer circumferential surface at the second end of the first ring segment and a latch rod in the outer circumferential surface of the recess;
wherein the fastening member comprises a fastening plate hingedly coupled to the second end of the second ring segment member at a second hinge, the fastening plate being rotatable about the second hinge when the second end of the first ring segment member is in contact with the second end of the second ring segment member to form a ring shape;
wherein the fastening plate comprises a latch protrusion protruding from an inner surface thereof, the latch protrusion being configured to latch with the latch rod of the first ring segment;
wherein a straight line connecting the first hinge to the second end of the fastening member forms a centerline of the ring shape formed by the first and second ring segment members.

7. The ring for enhancing male functions according to claim 6, wherein the first ring segment member further comprises a location checking portion formed on the second end thereof for informing of a direction in which the fastening member is latched to the first ring segment member.

8. A ring for enhancing male functions, comprising:
a first ring segment member comprising a plurality of first bosses protruding inward from a first inner circumferential surface thereof and a first groove formed between adjacent first bosses, the adjacent first bosses and the first groove adjoining each other on the first inner circumferential surface to form a wave shape, at least one of the first bosses including a first slope from a first rear end towards a root of a penis to a first protruding point and a second slope from a first front end towards glans to the first protruding point, the first slope being greater than the second slope, and the first protruding point being located closer to the first rear end than to the first front;
a second ring segment member rotatably coupled at a first end thereof to a first end of the first ring segment member, second ring segment comprising a plurality of second bosses protruding inward from a second inner circumferential surface thereof and a second groove formed between adjacent second bosses, the adjacent second bosses and the second groove adjoining each other on the second inner circumferential surface to form a wave shape, at least one of the second bosses including a third slope from a second rear end towards the root of the penis to a second protruding point and a fourth slope from a second front end towards the glans to the second protruding point, the third slope being greater than the fourth slope, and the second protruding point being located closer to the second rear end than to the second front end; and
a fastening member rotatably provided to a second end of the second ring segment member and detachably coupled to a second end of the first ring segment member, the fastening member being rotatable about a hinge when the second end of the first ring segment member is in contact with the second end of the second ring segment member to form a ring shape.

* * * * *